(12) United States Patent
Hintermann et al.

(10) Patent No.: US 7,087,756 B2
(45) Date of Patent: Aug. 8, 2006

(54) ISOXAZOLOPYRIDINONES

(75) Inventors: Samuel Hintermann, Basel (CH); Bastian Hengerer, Ulm (DE); Ulrike Von Krosigk, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/486,569

(22) PCT Filed: Aug. 14, 2002

(86) PCT No.: PCT/EP02/09134

§ 371 (c)(1),
(2), (4) Date: Jul. 23, 2004

(87) PCT Pub. No.: WO03/015780

PCT Pub. Date: Feb. 27, 2003

(65) Prior Publication Data

US 2004/0248893 A1    Dec. 9, 2004

(30) Foreign Application Priority Data

Aug. 15, 2001 (GB) .................... 0119911.6

(51) Int. Cl.
*C07D 471/02* (2006.01)
(52) U.S. Cl. ...................... 546/116; 546/115
(58) Field of Classification Search ............... 546/116, 546/115; 544/362; 514/302, 253.04
See application file for complete search history.

(56) References Cited

U.S. PATENT DOCUMENTS

| 4,049,813 A | 9/1977 | Nadelson |
| 4,064,251 A | 12/1977 | Nadelson |
| 4,113,727 A * | 9/1978 | Denzer et al. ............ 544/362 |
| 4,158,735 A | 6/1979 | Nadelson |
| 4,238,616 A | 12/1980 | Nadelson |
| 2004/0176407 A1* | 9/2004 | Nakamura et al. ......... 514/302 |

FOREIGN PATENT DOCUMENTS

| GB | 1545575 | 5/1979 |
| WO | WO 2002102807 A1 * | 12/2002 |

OTHER PUBLICATIONS

Castro et al. J. Biol. Chem. 1999, 274(52): 37483-37490.*
Wallen et al, Transcriptional Control of Dopamine Neuron Development, Ann. N.Y. Acad. Sci. 991: 48-60 (2003).*
Montastruc et al ,New Directions in the drug treatment of Parkinson's disease, PMID:8877311.*
Quinn, Drug Treatment of Parkinson's disease. PMID: 7888935.*

* cited by examiner

*Primary Examiner*—Amelia A. Owens
(74) *Attorney, Agent, or Firm*—Peter J. Waibel; E. Jay Wilusz

(57) ABSTRACT

The invention provides compounds of formula I, wherein X, Y, $R_1$, $R_2$, and $R_3$ are as defined in the description, and the preparation thereof. The compounds of formula I are useful as pharmaceuticals.

2 Claims, No Drawings

ISOXAZOLOPYRIDINONES

The present invention relates to novel isoxazolopyridinone derivatives, their preparation, their use as pharmaceuticals and pharmaceutical compositions containing them.

The invention provides compounds of formula I

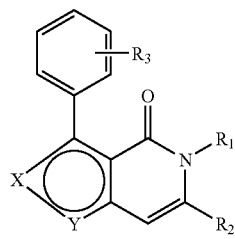

wherein
either X is O and Y is N or X is N and Y is O,
$R_1$ is hydrogen, $C_{1-4}$alkyl, $C_{3-7}$cycloalkyl, $C_{3-7}$cycloalkyl-$C_{1-4}$alkyl or di-$C_{1-4}$alkylamino-$C_{1-4}$alkyl,
$R_2$ is $C_{1-4}$alkyl, $C_{3-7}$cycloalkyl, benzo [1,3]dioxol-5-yl, benzo[1,2,5]oxadiazol-5-yl, benzo[1,2,5]thiadiazol-5-yl or a group of formula (a)

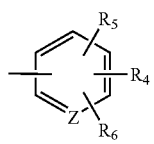

wherein Z is CH or N, $R_4$ is hydrogen, $C_{1-4}$alkyl, $C_{1-4}$alkoxy, halogen, hydroxy, trifluoromethyl, di-$C_{1-4}$alkylamino, $C_{1-4}$alkylamino, di-$C_{1-4}$alkylamino-$C_{1-4}$alkyl, $C_{1-4}$alkylamino-$C_{1-4}$alkyl, di-$C_{1-4}$alkylamino-$C_{1-4}$alkoxy, $C_{1-4}$alkylamino-$C_{1-4}$alkoxy, di-$C_{1-4}$ alkyl amino-$C_{1-4}$alkoxy-$C_{1-4}$alkyl, $C_{1-4}$alkylamino-$C_{1-4}$alkoxy-$C_{1-4}$alkyl, di-($C_{1-4}$alkoxy-$C_{1-4}$alkyl)amino, di-($C_{1-4}$alkoxy-$C_{1-4}$alkyl)amino-$C_{1-4}$alkyl, phenyl, phenoxy, benzyloxy $C_{1-4}$alkyl, $C_{1-4}$alkoxy-$C_{1-4}$alkyl, $C_{1-4}$alkoxy-$C_{1-4}$alkoxy-$C_{1-4}$alkyl, hydroxy-$C_{1-4}$alkyl, CHO, carboxy, $C_{1-4}$alkoxycarbonyl, morpholinomethyl, 4-$C_{1-4}$alkyl-piperazinylmethyl, piperazinylmethyl, tetrazol-1-ylmethyl, 1-pyrrolylmethyl, 3-(di-$C_{1-4}$-alkylamino-2-hydroxy-propoxy-$C_{1-4}$alkyl, 3-(di-$C_{1-4}$-alkylamino-2-hydroxy-propoxy, 3-$C_{1-4}$-alkylamino-2-hydroxy-propoxy-$C_{1-4}$alkyl, 3-$C_{1-4}$-alkylamino-2-hydroxy-propoxy, 2-hydroxy-3-imidazol-1-yl-propoxy-$C_{1-4}$alkyl, 2-hydroxy-3-imidazol-1-yl-propoxy, 2-hydroxy-3-morpholin-4-yl-propoxy, 2-hydroxy-3-morpholin-4-yl-propoxy-$C_{1-4}$alkyl, and $R_5$ and $R_6$, independently, are hydrogen, halogen, hydroxy, $C_{1-4}$alkyl or $C_{1-4}$alkoxy, and
$R_3$ is hydrogen, halogen, $C_{1-4}$alkyl, di-$C_{1-4}$alkylamino-$C_{1-4}$alkyl, di-$C_{1-4}$alkylamino-$C_{1-4}$alkoxy, $C_{1-4}$alkylamino-$C_{1-4}$ alkyl, $C_{1-4}$alkylamino-$C_{1-4}$alkoxy or $C_{1-4}$alkoxy, in free base or pharmaceutically acceptable acid addition salt form, for use in the treatment of Parkinson's disease.

Any alkyl or alkoxy group as defined above preferably has one or two carbon atoms and more preferably is methyl or methoxy.

Halogen denotes fluorine, chlorine or bromine.

In a further aspect, the invention provides a process for the production of the compounds of formula I and their salts, comprising the step of reacting a compound of formula II

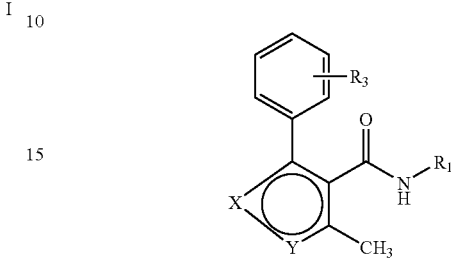

wherein $R_1$ and $R_3$ are as defined above, with a compound of formula III $$R_7—R_2 \quad\quad III$$

wherein $R_2$ is as defined above and $R_7$ is CHO, CN, CO-Hal, wherein Hal is halogen, CON($CH_3$)—$OCH_3$ or morpholinocarbonyl.

The reaction can be effected according to known methods, for example as described in Example 1 b).

Compounds of formula I wherein $R_2$ is a group of formula (a) wherein $R_4$ is di-$C_{1-4}$ alkylaminomethyl, $C_{1-4}$alkoxymethyl, di-$C_{1-4}$alkylamino-$C_{2-4}$alkoxymethyl, $C_{1-4}$alkoxy $C_{2-4}$alkoxymethyl, morpholinomethyl, piperazinylmethyl, 4-$C_{1-4}$alkylpiperazinylmethyl, tetrazol-1-ylmethyl or 1-pyrrolylmethyl, can also be produced from the corresponding compounds wherein $R_4$ is methyl, by bromination followed by nucleophilic substitution, according to conventional procedures, e.g. as described in Example 29.

Working up the reaction mixtures and purification of the compounds thus obtained may be carried out in accordance to known procedures.

Acid addition salts may be produced from the free bases in known manner, and vice-versa.

The starting compounds of formula II may be produced from carboxylic acids of formula IV

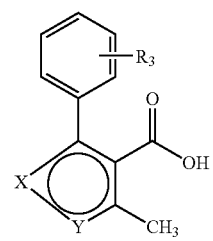

wherein X, Y and $R_3$ are as defined above, according to known procedures, e.g. as described in Example 1a).

The starting materials of formulae III and IV are known or may be produced in analogous manner to known procedures.

Compounds of formula I and their pharmaceutically acceptable acid addition salts, hereinafter referred to as agents of the invention, exhibit valuable pharmacological properties where tested in vitro using Nurr1 expressing cell cultures and in vivo, and are therefore useful as pharmaceuticals.

The nuclear receptor Nurr1 is known to be causally involved in the functional differentiation of midbrain dopaminergic neurones both during development and in adult animals. The defects of dopaminergic neurones observed in the ventral midbrain of Nurr1 knockout animals resemble the pattern of neuronal degeneration in Parkinson's disease, in which the primary motor defects are caused by the degeneration of the substantia nigra dopaminergic system (Zetterström et al., 1997; Castillo et al., 1998 and Saucedo-Cardenas et al., 1998). Nurr1 activators are therefore suggested for preventing or delaying the onset of Parkinsonian symptoms.

The affinity of the agents of the Invention to the Nurr1 receptor can be determined in vitro in binding studies:

Two-dimensional $^1H$-$^{15}N$ correlated spectra (HSQC) are recorded of uniformly $^{15}N$-labeled ligand binding domain (LBD) of Nurr1 expressed in E. Coli. The spectra provide a fingerprint of the protein structure and changes in the exact positions of some of the cross peaks in the 2-d spectrum upon titration of a compound indicate ligand binding.

In this assay, changes in chemical shift are observed in some peaks at concentrations of 300 µM of the agent of the invention, using 50 µM uniformly $^{15}N$-labeled Nurr1 LBD.

The activity of the agents of the invention at the Nurr1 receptor can be determined in vitro in cellular assays:

Induction of the biological activity of the Nurr1 receptor by the agents of the invention can be measured by the transactivation of a Nurr1 responsive reporter gene in a midbrain dopaminergic cell line. The assay is based on the transcription promoting effect of Nurr1. The reporter gene can be activated both by Nurr1 monomers and Nurr1/RXR heterodimers. RXR is a frequent heterodimerisation partner of nuclear receptors and it has been shown that Nurr1 can form heterodimers with RXR (Zetterström RH et al. Mol. Endocrinol. 1996; 10:1656–1666).

In this assay the agents of the invention significantly increase the reporter gene activity dose dependently at $EC_{50}$s of about 1 to about 100 nM.

In vivo, the agents of the invention significantly increase midbrain dopamine levels at doses of 5 to 30 mg/kg p.o. in the following assay:

OF1 mice are treated with the test compound for five days and sacrificed 5 hours after the last compound application. Dopamine levels are measured in substantia nigra and striatal tissue punches. 10 animals are treated in each group.

The agents of the invention are therefore useful in the treatment of Parkinson's disease.

For the above-mentioned indication, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 500, preferably from about 0.5 to about 100 mg/kg animal body weight. In larger mammals, for example humans, an indicated daily dosage is in the range from about 1 to about 500, preferably from about 1 to about 300 mg of an agent of the invention, conveniently administered, for example, in divided doses up to four times a day or in sustained release form.

The agents of the invention may be administered in free form or in pharmaceutically acceptable salt form. Such salts may be prepared in conventional manner and exhibit the same order of activity as the free compounds.

The agent of the invention may be administered by any conventional route, in particular enterally, preferably orally, for example in the form of tablets or capsules, or parenterally, for example in the form of injectable solutions or suspensions.

The agents of the invention may alternatively be administered e.g. topically in the form of a cream, gel or the like, or by inhalation, e.g. in dry powder form.

Examples for compositions comprising an agent of the invention include, e.g. a solid dispersion, an aqueous solution, e.g. containing a solubillising agent, a microemulsion and a suspension of an agent of the invention. The composition may be buffered to a pH in the range of e.g. from 3.5 to 9.5, by a suitable buffer.

The agents of the invention can be administered either alone or in combination with other pharmaceutical agents effective in the treatment of Parkinson's disease.

Thus, the agents of the invention can be used for the treatment of Parkinson's disease in combination with, for example, dopamine precursors (e.g. different levodopa preparations), dopamine agonists (e.g. Bromocriptine, Pramipexole), catechol-O-methyltransferase inhibitors (e.g. Entacapone, Tolcapone), monoamine oxidase B inhibitors (e.g. Selegiline), NMDA antagonists (e.g. Amantadine) and anticholinergics (e.g. Biperiden, Orphenedrine).

In accordance with the foregoing, the present invention also provides the use of an agent of the Invention, for the manufacture of a medicament for the treatment of Parkinson's disease.

The preferred agents of the invention include 6-(4-dimethylaminomethyl-phenyl)-3-phenyl-5H-isoxazolo[4,5-c]pyridin-4-one and 6-[4-(2-methoxy-ethoxymethyl)-phenyl]-5-methyl-3-phenyl-5H-isoxazolo[4,5-c]pyridin-4-one, in free base or pharmaceutically acceptable acid addition salt form.

In the above-mentioned in vitro cellular assay, these compounds increase the reporter gene activity with $EC_{50}$s of 70 and 40 nM respectively. In the above-mentioned in vivo test, they increase the dopamine levels by about 20–30% on administration of 5, 10 and 30 mg/kg p.o.

In still a further aspect, the invention provides compounds of formula I wherein X, Y, $R_1$, $R_2$ and $R_3$ are as defined above, provided that i) when X is N, Y is O, $R_2$ is unsubstituted phenyl and $R_3$ is hydrogen, then $R_1$ is different from hydrogen, and ii) when X is N, Y is O, $R_2$ is a group of formula (a) wherein either Z is N and $R_4$ is hydrogen, or Z is CH and $R_4$ is hydrogen, methyl, methoxy, halogen, trifluoromethyl, p-bromomethyl, p-benzyloxy, dimethylaminomethyl, methylaminomethyl, 4-$C_{1-4}$alkylpiperazinomethyl, piperidinomethyl or morpholinomethyl and $R_3$ is hydrogen, chlorine, fluorine, methyl, trifluoromethyl or $C_{1-4}$alkoxy, then $R_1$ is different from methyl, hereinafter referred to as novel compounds of formula I.

The present invention furthermore provides a pharmaceutical composition comprising a novel compound of formula I in free base or pharmaceutically acceptable acid addition salt form, in association with at least one pharmaceutical carrier or diluent. Such compositions may be manufactured in conventional manner. Unit dosage forms contain, for example, from about 0.25 to about 150, preferably from 0.25 to about 25 mg of the compound.

The pharmaceutical compositions for separate administration of the combination partners and for the administration in a fixed combination, i.e. a single galenical composition comprising at least two combination partners according to the invention, can be prepared in a manner known per se and are thus suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

In particular, a therapeutically effective amount of each of the combination partners may be administered simultaneously or sequentially and in any order, and the components may be administered separately or as fixed combination.

Accordingly the invention also provides a combination comprising a therapeutically effective amount of a novel compound of formula I in free base or pharmaceutically acceptable acid addition salt form and a second drug substance, said second drug substance being for example for use in Parkinson's disease.

Moreover the present invention provides the use of a novel compound of formula I in free base or pharmaceutically acceptable acid addition salt form, as pharmaceutical for the treatment of Parkinson's disease.

In still a further aspect the present invention provides a method for the treatment of Parkinson's disease in a subject in need of such treatment, which comprises administering to such subject a therapeutically effective amount of a novel compound of formula I in free base or pharmaceutically acceptable acid addition salt form.

The following examples illustrate the invention.

EXAMPLE 1

5-Methyl-6-[4-(4-methyl-piperazin-1-ylmethyl)-phenyl]-3-phenyl-5H-isoxazolo[4,5-c]pyridin-4-one a) 5-Methyl-3-phenyl-isoxazole-4-carboxylic acid methylamide To a suspension of 50.0 g (0.25 mol) of 5-methyl-3-phenyl-isoxazole-4-carboxylic acid in 1.2 l of 1,2-dichloroethane (DCE) is added 1.9 ml dimethyl formamide (DMF) and 21.4 ml (0.3 mol, 1.2 eq.) of thionyl chloride. The mixture is stirred for 2 h at reflux until a clear, yellow solution is formed. The solution is cooled to room temperature and then slowly added to a 8M solution of methylamine in ethanol (146 ml) at 5° C. The suspension is poured onto methylene chloride, washed with sat. NaHCO$_3$-solution, dried over Na$_2$SO$_4$ and concentrated. This yields 52.3 g (99%) of the title compound as light brown solid, which is used for further reaction without purification. Mass spectrum: m/z (M+H)$^+$: 217.1 b) 5-Methyl-6-[4-(4-methyl-piperazin-1-ylmethyl)-phenyl]-3-phenyl-5H-isoxazolo[4,5-c]pyridin-4-one In a 500 ml flask, 10.0 g (46.3 mmol) of 5-methyl-3-phenyl-isoxazole-4-carboxylic acid methylamide is suspended in 150 ml of tetrahydrofuran (THF) under argon. At −70° C. a solution of butyl lithium (63 ml, 1.6M in hexane, 101 mmol, 2.2 eq.) is slowly added. After 1 h at this temperature, the solution is warmed to −10° C. and a solution of 11.9 g (55.5 mmol, 1.2 eq.) of 4-(4-methyl-piperazin-1-ylmethyl)-benzonitrile in 80 ml of THF is slowly added. Under warming to room temperature, the red solution is stirred for another hour, then quenched with 2 ml of water and concentrated. The yellow residue is then taken up in 75 ml of dioxane and kept at 5° C. Then, 230 ml of a 4M solution of HCl in dioxane is carefully added and the suspension stirred for 20 h at room temperature. Then, the solvent is removed and the residue dissolved in ethyl acetate and carefully neutralised with sat. NaHCO$_3$-solution. The phases are separated and the organic phases washed with brine, dried over Na$_2$SO$_4$ and concentrated. Chromatographic purification (CH$_2$Cl$_2$/MeOH 95:5 to 90:10) yields 7.9 g (41%) of 5-methyl-6-[4-(4-methyl-piperazin-1-ylmethyl)-phenyl]-3-phenyl-5H-isoxazolo[4,5-c]pyridin-4-one as a white solid. Mass spectrum: m/z (M+H)$^+$: 415.0

According to the procedure described for Example 1, using the appropriate nitrile or Weinreb Amide, the following compounds are prepared:

EXAMPLE 2

6-Benzo[1,3]dioxol-5-yl-5-methyl-3-phenyl-5H-isoxazolo[4,5-c]pyridin-4-one: This compound is obtained using benzo[1,3]dioxole-5-carbonitrile in 56% as a light yellow solid. Mass spectrum: m/z (M+H)$^+$: 347.2

EXAMPLE 3

6-Biphenyl-4-yl-5-methyl-3-phenyl-5H-isoxazolo[4,5-c]pyridin-4-one: This compound is obtained using biphenyl-4-carbonitrile in 11% as a white foam. Mass spectrum: m/z (M+H)$^+$: 379.1

EXAMPLE 4

5-Methyl-3-phenyl-6-pyridin-4-yl-5H-isoxazolo[4,5-c]pyridin-4-one: This compound is obtained using isonicotinonitrile in 59% as a pink solid. Mass spectrum: m/z (M+H)$^+$: 304.1

EXAMPLE 5

6-(4-Diethylamino-phenyl)-5-methyl-3-phenyl-5H-isoxazolo[4,5-c]pyridin-4-one: This compound is obtained using 4-diethylamino-benzonitrile in 11% as a beige solid. Mass spectrum: m/z (M+H)$^+$: 374.1

EXAMPLE 6

5-Methyl-6-(4-phenoxy-phenyl)-3-phenyl-5H-isoxazolo[4,5-c]pyridin-4-one: This compound is obtained using 4-phenoxy-benzonitrile in 44% as a beige solid. Mass spectrum: m/z (M+H)$^+$: 395.0

EXAMPLE 7

6-[4-(2-Methoxy-ethoxymethyl)-phenyl]-5-methyl-3-phenyl-5H-isoxazolo[4,5-c]pyridin-4-one: This compound is obtained using N-Methoxy-4-(2-methoxy-ethoxymethyl)-N-methyl-benzamide in 58% as a white solid. Mass spectrum: m/z (M+H)$^+$: 391.2

EXAMPLE 8

5-Methyl-3-phenyl-6-(4-tetrazol-1-ylmethyl-phenyl)-5H-isoxazolo[4,5-c]pyridin-4-one: This compound is obtained using 4-tetrazol-1-ylmethyl-benzonitrile and after additional RP18-purification in 6% as a white solid. Mass spectrum: m/z (M-N$_2$+H)$^+$: 357.1

EXAMPLE 9

5-Methyl-3-phenyl-6-p-tolyl-5H-isoxazolo[4,5-c]pyridin-4-one: This compound is obtained using 4-methyl-benzonitrile in 56% as a beige solid. Mass spectrum: m/z (M+H)$^+$: 317.1

EXAMPLE 9a 6-(3,4-Dimethoxy-phenyl)-5-methyl-3-phenyl-5H-isoxazolo[5-c]pyridin-4-one: This compound is obtained using 3,4-dimethoxy-benzonitrile in 11% as a beige solid. Mass spectrum: m/z (M+H)$^+$: 363.1

EXAMPLE 9b 6-(3,5-Dimethoxy-phenyl)-5-methyl-3-phenyl-5H-isoxazolo[4,5-c]pyridin-4-one: This compound is obtained using 3,5-dimethoxy-benzonitrile in 25% as a yellow resin. Mass spectrum: m/z (M+H)$^+$: 363.1

According to the procedure described for Example 1, using acetylchloride instead of the nitrile, the following compound is prepared:

EXAMPLE 10

5,6-Dimethyl-3-phenyl-5H-isoxazolo[4,5-c]pyridin-4-one: Mass spectrum: m/z (M+H)$^+$: 241.2

According to the procedure described for example 1, using the appropriate nitrile or Weinreb Amide, 5-methyl-3-phenyl-isoxazole-4-carboxylic acid amide and 3.3 eq. of butyl lithium, the following compounds are prepared:

EXAMPLE 11

6-(4-Dimethylaminomethyl-phenyl)-3-phenyl-5H-isoxazolo[4,5-c]pyridin-4-one: This compound is obtained using 4-dimethylaminomethyl-benzonitrile in 25% as a beige solid. Mass spectrum: m/z (M+H)$^+$: 346.2

EXAMPLE 12

6-[4-(4-Methyl-piperazin-1-ylmethyl)-phenyl]-3-phenyl-5H-isoxazolo[4,5-c]pyridin-4-one: This compound is obtained using 4-(4-methyl-piperazin-1-ylmethyl)-benzonitrile in 13% as a solid. Mass spectrum: m/z (M+H)$^+$: 401.1

EXAMPLE 13

6-[4-(2-Methoxy-ethoxymethyl)-phenyl]-3-phenyl-5H-isoxazolo[4,5-c]pyridin-4-one: This compound is obtained using N-Methoxy-4-(2-methoxy-ethoxymethyl)-N-methyl-benzamide in 70% as a white solid. Mass spectrum: m/z (M+H)$^+$: 377.1

According to the procedure described for example 1, using the appropriate nitrile and 5-methyl-3-phenyl-isoxazole-4-carboxylic acid ethylamide, the following compounds are prepared:

EXAMPLE 14

5-Ethyl-6-(3-methoxy-phenyl)-3-phenyl-5H-isoxazolo[4,5-c]pyridin-4-one: This compound is obtained using 3-methoxy-benzonitrile in 28% as a solid. Mass spectrum: m/z (M+H)$^+$: 347.2

EXAMPLE 15

6-Benzol[1,3]dioxol-5-yl-5-ethyl-3-phenyl-5H-isoxazolo[4,5-c]pyridin-4-one: This compound is obtained using benzo[1,3]dioxole-5-carbonitrile in 10% as a solid. Mass spectrum: m/z (M+H)$^+$: 361.2

According to the procedure described for example 1, using the appropriate nitrile and 5-methyl-3-phenyl-isoxazole-4-carboxylic acid propylamide, the following compound is prepared:

EXAMPLE 16

3,6-Diphenyl-5-propyl-5H-isoxazolo[4,5-c]pyridin-4-one: This compound is obtained using benzonitrile in 49% as a solid. Mass spectrum: m/z (M+H)$^+$: 331.2

According to the procedure described for example 1, using the appropriate nitrile and 5-methyl-3-phenyl-isoxazole-4-carboxylic acid cyclopropylamide, the following compounds are prepared:

EXAMPLE 17

5-Cyclopropyl-3,6-diphenyl-5H-isoxazolo[4,5-c]pyridin-4-one: This compound is obtained using benzonitrile in 17% as a solid. Mass spectrum: m/z (M+H)$^+$: 329.2

EXAMPLE 18

6-Benzo[1,3]doxol-5-yl-5-cyclopropyl-3-phenyl-5H-isoxazolo[4,5-c]pyridin-4-one: This compound is obtained using benzo[1,3]dioxole-5-carbonitrile in 12% as a solid. Mass spectrum: m/z (M+H)$^+$: 373.2

EXAMPLE 19

5-Methyl-3,6-diphenyl-5H-isoxazolo[4,3-c]pyridin-4-one a) 3-Methyl-5-phenyl-isoxazole-4-carboxylic acid methylamide To a suspension of 6.0 g (29.6 mmol) of 3-methyl-5-phenyl-isoxazole-4-carboxylic acid in 150 ml DCE is added 0.3 ml of DMF and 2.6 ml (35.5 mmol, 1.2 eq.) of thionyl chloride. The mixture is stirred for 2 h at reflux until a brown solution is formed. The solution is cooled to room temperature and then slowly added to a 8M solution of methylamine in ethanol (18 ml) at 5° C. The suspension is poured onto methylene chloride, washed with sat. NaHCO$_3$-solution, dried over Na$_2$SO$_4$ and concentrated. This yields 6.7 g (quant.) of the title compound as brown solid, which is used for further reactions without purification. Mass spectrum: m/z (M+H)$^+$: 217.2 b) 5-Methyl-3,6-diphenyl-5H-isoxazolo[4,3-c]pyridin-4-one 159 mg (0.73 mmol) of 3-methyl-5-phenyl-isoxazole-4-carboxylic acid methylamide is suspended in 4 ml of THF under argon. At −5° C. a solution of butyl lithium (1.0 ml, 1.6M in hexane, 1.6 mmol, 2.2 eq.) is slowly added. After 1 h at this temperature, the solution is warmed to 0° C. and 0.92 ml (0.88 mmol, 1.2 eq.) of benzonitrile is slowly added. Under warming to room temperature, the red solution is stirred for another 2 h, then quenched with 0.1 ml of water and concentrated. The residue is then taken up in 4 ml of a 4M solution of HCl in dioxane and the suspension stirred for 16 h at room temperature. Then, the solvent is removed and the residue dissolved in ethyl acetate and carefully neutralised with sat. NaHCO$_3$-solution. The phases are separated and the organic phases washed with brine, dried over Na$_2$SO$_4$ and concentrated. Chromatographic purification (hexane/ethyl acetate 90:10) yields 108 mg (48%) of 5-methyl-3,6-diphenyl-5H-isoxazolo[4,3-c]pyridin-4-one as a white solid. Mass spectrum: m/z (M+H)$^+$: 303.2

According to the procedure described for example 19, using the appropriate nitrile, the following compounds are prepared:

EXAMPLE 20

6-(4-Chloro-phenyl)-5-methyl-3-phenyl-5H-isoxazolo[4,3-c]pyridin-4-one: This compound is obtained using 4-chloro-benzonitrile in 54% as a solid. Mass spectrum: m/z (M+H)$^+$: 337.2, 339.3

EXAMPLE 21

5-Methyl-6-[4-(4-methyl-piperazin-1-ylmethyl)-phenyl]-3-phenyl-5H-isoxazolo[4,3-c]pyridin-4-one: This compound is obtained using 4-(4-methyl-piperazin-1-ylmethyl)-benzonitrile in 8% as a solid. Mass spectrum: m/z (M+H)$^+$: 415.3

According to the procedure described for example 19, using the appropriate nitrile, 3-methyl-5-phenyl-isoxazole-4-carboxylic acid amide and 3.3 eq. of butyl lithium, the following compounds are prepared:

EXAMPLE 22

6-(4-Dimethylaminomethyl-phenyl)-3-phenyl-5H-isoxazolo[4,3-c]pyridin-4-one: This compound is obtained using 4-dimethylaminomethyl-benzonitrile in 9% as a brown solid. Mass spectrum: m/z (M+H)$^+$: 346.2

EXAMPLE 23

6-[4-(4-Methyl-piperazin-1-ylmethyl)-phenyl]-3-phenyl-5H-isoxazolo[4,3-c]pyridin-4-one: This compound is obtained using 4-(4-Methyl-piperazin-1-ylmethyl)-benzonitrile in 9% as a beige solid. Mass spectrum: m/z (M+H)$^+$: 401.2

EXAMPLE 24

6-(2,4-Dimethoxy-phenyl)-5-methyl-3-phenyl-5H-isoxazolo[4,5-c]pyridin-4-one: To a solution of 216 mg (1.0 mmol) of 5-methyl-3-phenyl-isoxazole-4-carboxylic acid methylamide in 5 ml of THF are slowly added 1.4 ml of butyl lithium (1.6M in hexane, 2.2 mmol, 2.2 eq.) at −40° C. The orange suspension is stirred under warming to room temperature for 1 h. Then, at 0° C. 300 mg (1.2 mmol, 1.2 eq.) of 2,4-dimethoxy-benzaldehyde is added and the mixture stirred for another hour under warming to room temperature. The mixture is quenched with 0.1 ml of water and the solvents are removed under reduced pressure. The residue is taken up in CH$_2$Cl$_2$, washed with sat. NaHCO$_3$-solution, dried over Na$_2$SO$_4$ and concentrated. Purification by flash chromatography yields 278 mg of a white foam.

This intermediate is dissolved in 5 ml of acetone, treated with 0.55 ml of Jones' reagent (1.1 mmol) and stirred at room temperature for 24 h. The mixture is taken up in CH$_2$Cl$_2$ and the phases are separated, the aqueous phases is extracted 2 times with CH$_2$Cl$_2$, the combined organic phases washed with brine and dried over Na$_2$SO$_4$ and the solvent removed in vacuo. The residue is then purified over silica gel (hexane/ethyl acetate 8:2 to 1:1) to yield 154 mg (43%) of the title compound as white solid. Mass spectrum: m/z (M+H)$^+$: 363.1

According to the procedure described for example 24, using the appropriate isoxazoles and aldehydes, the following compounds are prepared:

EXAMPLE 25

6-Cyclohexyl-5-methyl-3-phenyl-5H-isoxazolo[4,5-c]pyridin-4-one: This compound is obtained using 5-methyl-3-phenyl-isoxazole-4-carboxylic acid methylamide and cyclohexanecarbaldehyde in 40% as a beige solid. Mass spectrum: m/z (M+H)$^+$: 309.0

EXAMPLE 25a 6-(2,4-Dimethoxy-phenyl)-5-methyl-3-phenyl-5H-isoxazolo[4,5]pyridin-4-one: This compound is obtained using 5-methyl-3-phenyl-isoxazole-4-carboxylic acid methylamide and 2,4-dimethoxy-benzaldehyde in 42% as a white solid. Mass spectrum: m/z (M+H)$^+$: 363.1

EXAMPLE 26

4-(5-Methyl-4-oxo-3-phenyl-4,5-dihydro-isoxazolo[4,3-c]pyridin-6-yl)-benzoic acid methyl ester: This compound is obtained using 3-methyl-5-phenyl-isoxazole-4-carboxylic acid methylamide and 4-formyl-benzoic acid methyl ester in 15% as a beige solid. Mass spectrum: m/z (M+H)$^+$: 361.2

EXAMPLE 27

6-Benzo[1,3]dioxol-5-yl-3-(2-chloro-phenyl)-5-methyl-5H-isoxazolo[4,5-c]pyridin-4-one: This compound is obtained using 3-(2-chloro-phenyl)-5-methyl-isoxazole-4-carboxylic acid methylamide and benzo[1,3]dioxole-5-carbaldehyde in 35% as a beige solid. Mass spectrum: m/z (M+H)$^+$: 380.9, 382.9

EXAMPLE 28

6-Cyclohexyl-5-ethyl-3-phenyl-5H-isoxazolo[4,5-c]pyridin-4-one: This compound is obtained using 5-methyl-3-phenyl-isoxazole-4-carboxylic acid ethylamide and cyclohexanecarbaldehyde in 20% as a solid. Mass spectrum: m/z (M+H)$^+$: 323.3

EXAMPLE 29

5-Methyl-3-phenyl-6-(4-pyrrol-1-ylmethyl-phenyl)-5H-isoxazolo[4,5-c]pyridin-4-one a) 6-(4-Bromomethyl-phenyl)-5-methyl-3-phenyl-5H-isoxazolo[4,5-c]pyridin-4-one: At room temperature, 640 mg (2.0 mmol) of 5-methyl-3-phenyl-6-p-tolyl-5H-isoxazolo[4,5-c]pyridin-4-one is dissolved in 40 ml of CCl$_4$. After addition of 34 mg (0.2 mmol, 0.1 eq.) of azoisobutyronitrile, the reaction is heated to reflux and stirred for 16 h. After cooling to room temperature, the suspension is taken up in CH$_2$Cl$_2$ and washed with 0.1M NaHSO$_3$-solution and sat. NaHCO$_3$-solution, dried over Na$_2$SO$_4$ and the solvent removed in vacuo to yield 1.1 g (crude, quant.) of a foam, which is used for further reaction without purification. Mass spectrum: m/z (M+H)$^+$: 394.9, 396.9 b) 5-Methyl-3-phenyl-6-(4-pyrrol-1-ylmethyl-phenyl)-5H-isoxazolo[4,5-c]pyridin-4-one To a solution of 198 mg (0.5 mmol) of 6-(4-bromomethyl-phenyl)-5-methyl-3-phenyl-5H-isoxazolo[4,5-c]pyridin-4-one in 2.5 ml of DMF is added 326 mg (1.0 mmol, 2.0 eq.) of caesium carbonate and 0.05 ml (0.6 mmol, 1.2 eq.) of pyrrole. After stirring 16 h at room temperature the solvent is removed in vacuo and the residue taken up in $CH_2Cl_2$. The organic phase is washed with $NaHCO_3$-solution, dried over $Na_2SO_4$ and concentrated. Flash chromatography yields 34 mg (18%) of the desired compound as a white solid. Mass spectrum: m/z (M+H)$^+$: 382.1

According to the procedure described for example 29, replacing pyrrole by the appropriate nucleophile, the following examples are prepared:

EXAMPLE 30

6-(4-Benzyloxymethyl-phenyl)-5-methyl-3-phenyl-5H-isoxazolo[4,5-c]pyridin-4-one: This compound is obtained using benzyl alcohol in 18% as a white solid. Mass spectrum: m/z (M+H)$^+$: 423.0

EXAMPLE 31

6-(4-Methoxymethyl-phenyl)-5-methyl-3-phenyl-5H-isoxazolo[4,5-c]pyridin-4-one: This compound is obtained using methanol in 27% as a white solid. Mass spectrum: m/z (M+H)$^+$: 347.3

EXAMPLE 32

6-[4-(2-Hydroxy-ethoxymethyl)-phenyl]-5-methyl-3-phenyl-5H-isoxazolo[4,5-c]pyridin-4-one: This compound is obtained using 2-amino-ethanol in 20% as a white solid. Mass spectrum: m/z (M+H)$^+$: 404.1

EXAMPLE 33

6-[4-(2-Hydroxy-ethoxymethyl)-phenyl]-5-methyl-3-phenyl-5H-isoxazolo[4,5-c]pyridin-4-one: This compound is obtained using ethane-1,2-diol and potassium hydroxide as base in 35% as a clear oil. Mass spectrum: m/z (M+H)$^+$: 377.1

The invention claimed is:

1. 6-(4-Dimethylaminomethyl-phenyl)-3-phenyl-5H-isoxazolo[4,5-c]pyridine-4-one in free base or acid addition salt form.

2. 6-[4-(2-Methoxy-ethoxymethyl)-phenyl]-5-methyl-3-phenyl-5H-isoxazolo[4,5-c]pyridin-4-one in free base or acid addition salt form.

* * * * *